United States Patent
Kolta

(10) Patent No.: US 6,280,032 B1
(45) Date of Patent: Aug. 28, 2001

(54) SYSTEM FOR DETECTING AND CORRECTING COLOR VISION DEFICIENCIES BASED ON CRITICAL FUSION FREQUENCY SPECTRAL SCANNING

(76) Inventor: Peter Kolta, Littke u. 18., H-7632 Pécs (HU)

( * ) Notice: Subject to any disclaimer, the term of this patent is extended or adjusted under 35 U.S.C. 154(b) by 0 days.

(21) Appl. No.: 09/646,002

(22) PCT Filed: Mar. 5, 1999

(86) PCT No.: PCT/HU99/00018

§ 371 Date: Sep. 11, 2000

§ 102(e) Date: Sep. 11, 2000

(87) PCT Pub. No.: WO99/45836

PCT Pub. Date: Sep. 16, 1999

(30) Foreign Application Priority Data

Mar. 9, 1998 (HU) .................................................. 9800510

(51) Int. Cl.⁷ ........................................................ A61B 3/08

(52) U.S. Cl. .................................................................. 351/201

(58) Field of Search ...................................... 351/201, 200, 351/221, 238, 243, 222, 245; 349/78, 106

(56) References Cited

U.S. PATENT DOCUMENTS

| 3,814,510 | 6/1974 | Adler et al. . |
| 3,891,311 | * 6/1975 | Fletcher et al. ...................... 351/245 |
| 4,886,343 | * 12/1989 | Johnson ................................. 349/78 |
| 4,940,323 | 7/1990 | Downing . |
| 6,129,436 | * 10/2000 | Treskov et al. ...................... 351/201 |

FOREIGN PATENT DOCUMENTS

| 95/05621 | 2/1995 | (WO) . |
| 95/28125 | 10/1995 | (WO) . |

* cited by examiner

*Primary Examiner*—George Manuel
(74) *Attorney, Agent, or Firm*—Venable; Gabor J. Kelemen

(57) ABSTRACT

Method for detecting color vision deficiencies of a subject by determining his or her spectral sensitivity curve, wherein the spectral sensitivity curve is determined by critical fusion frequency spectral scanning at predetermined discrete narrow bands of wavelengths, preferably being blue, green, orange and red. The compensation of the color vision deficiency occurs by using a compensation color determined on the basis of differences between a standard sensitivity curve and the measured one. In each wavelength where such differences are experienced, the intensity of the light source generating that wavelength is increased or decreased in accordance with the extent and sign of the difference, and the compensation color is obtained by illuminating all light sources.

13 Claims, 6 Drawing Sheets

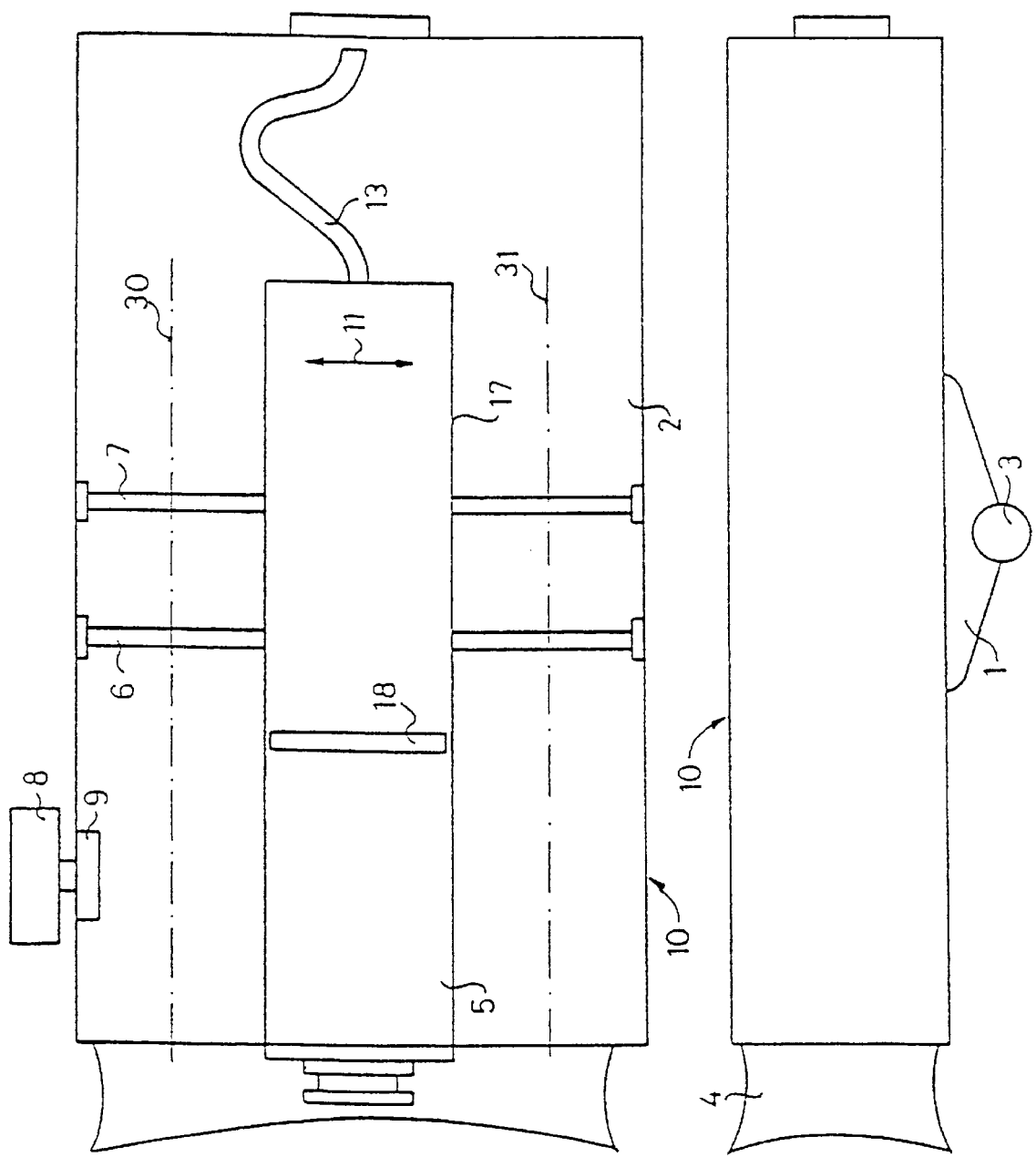

SYSTEM FOR DETECTING AND CORRECTING COLOR VISION DEFICIENCIES BASED ON CRITICAL FUSION FREQUENCY SPECTRAL SCANNING

The invention relates to a new method for determining the spectral sensitivity curve of the human vision system, to a new method for correcting color vision deficiencies and to respective apparatus for carrying out the methods, i.e. to color sensitivity measuring and correcting systems. The correcting system includes color glasses and lenses, as well as circuits by which the color image of a color display can be influenced to compensate the color vision deficiencies of a particular subject.

Color vision deficiencies are the result of non-uniform sensitivities of the different pigmented cones in the eyes of the subject; in other words such persons have spectral sensitivity curves differing from the standard curve characteristic of those with normal vision capabilities. There are certain diseases or disorders, wherein one or more pigmented types of cones are missing. Such persons are color blind, and physical devices cannot correct such deficiencies. As long as the subject has more than two types of cones with differing spectral sensitivities, color vision deficiencies can be corrected or compensated. A few percentages of color vision deficiencies have acquired nature, i.e. they are the result of certain diseases, and they can disappear when the basic disease is cured. It is often important for the practitioner to make distinction between inborn and acquired color vision deficiencies.

Different statistics report differing incidence rate for color deficiencies, and according to data reported in the 1996 edition of Encyclopaedia Britannica this rate is about 4% for men and 0.4% for women. If lighter (undetected) color vision problems are also taken into account, the actual occurrence rate is probably higher.

There are several empirical methods for determining color vision deficiencies, of which the most common one is the use of color tables comprising mosaic structures of color spots, i.e. pseudo isochromatic figures, which are chosen in such a way that a pattern is hidden therein. With normal vision the embedded patterns can well be recognised. The color structure is arranged in such a way that in case of most kinds of color vision deficiencies the subject under test cannot identify the embedded pattern in case of one or more specific tables. The practitioner can determine the fact and the type of color deficiencies based on the result of such tests. An example for such tables is the book of Karl Verhagen and Dieter Broschmann: "Tafeln und Prüfung des Farbensichtes" published by Georg Thieme Verlag, 1992 and its Hungarian translation by Medicina Kiadó, Budapest, 1992. The tests based on such tables should be carried out so that natural light should evenly illuminate the page under test and the light flux should be at least about 40–50 lux.

While this is the most widely used method for the detection of color vision deficiencies, it is inappropriate to detect color deficiencies caused by the sensitivity errors in the blue spectral range. Color tables cannot discover smaller problems in the color vision system as long as the subject is capable of recognizing the embedded pattern.

Color vision properties have been thoroughly analyzed by George Wald "The Receptors of Human Color Vision" and the appendix thereto by W. S. Stiles (Science, Vol. 145, September 1964, pp. 1007–1016). Wald has worked out a method for measuring the spectral sensitivity curves and reported his results of measurement. In addition he compared his results with the results of other researchers and compiled sensitivity curves of different origin for the most typical color vision deficiency types. It is beyond doubt that color vision deficiencies are truly reflected in the specific spectral sensitivity curve of the subject.

The exact mechanism of color vision is not yet known. In a model the color vision system is thought that cones have three different pigment types, and color vision is obtained by the processing of this information in the vision center of the brain. This theory cannot explain certain duality of the color vision deficiencies, i.e. where deficiencies are experienced in pairs of different colors i.e. red-green or blue-yellow. In the most advanced theory color vision is thought to be the result of two curves each including positive and negative chromatic values (Hurvich and Jameson, 1972). It is not the task of this specification to provide full theoretic background for color vision, but to focus the attention to the significance of the measurement of spectral sensitivity curves.

The methods of Wald and other authors for measuring the spectral sensitivity have not obtained wide acceptance, since they require long time and expensive instrumentation, furthermore apart from the scientific value; the knowledge of such curves has not served as basis for any practical therapeutic application.

Several authors have recognised that color vision deficiencies can be corrected by the use of color filters of specific spectral distribution. Hungarian patent 108.453 of Abraham et al. is based on the three-receptor theory and suggests that color vision deficiencies are the result of shifts in the respective spectral sensitivity curves. They determine the respective curves, provide the function of the deviations from the standard curves and apply combined filters that compensate for such shifts. The specification does not give a clear teaching how can the deviation function be established and how should the filter be made.

The primary object of the invention is to provide a new method for determining the spectral sensitivity curve of the human vision system in a fast and simple but reproducible way.

A further object of the present invention is to establish a color light which has a specific spectral distribution (i.e. color) capable of compensating the difference between the specific spectral sensitivity curve of a subject and the standard sensitivity curve associated with normal color vision.

A still further object is to provide an apparatus by which such sensitivity curves can be determined and which can provide the aforementioned compensating light.

It is also the object of the invention to provide a specific glass, which uses the compensating color as a filter and can provide thereby a normal color vision for the subject.

The last object of the invention is to provide a compensating system usable in a color display, that modifies the colors to be displayed in such a way that the subject with a specific color vision deficiency can see the picture with correct colors as if he had no deficiency.

According to the invention it has been recognised that the spectral sensitivity curve can be obtained by utilising a law known in a different field of the physiology of sensory reception i.e. the Ferry-Porter law. This law relates to a phenomenon called flicker, which is the sensation evoked when a visual stimulus is repeated rapidly. At low repetition rates the fluctuation can well be sensed, at higher rates the sensation becomes one of flicker - i.e., rapid fluctuations in brightness; finally, at a certain speed, called the critical fusion frequency, the sensation becomes continuous and the subject is unaware of the alterations in the illumination. At high levels of luminance, when cone vision is employed, the fusion frequency is high; increasing with increasing luminance in a logarithmic fashion and this is the Ferry-Porter law. From the above-cited paper of Wald it is known that the sensation of luminous intensity is a logarithmic function of the illumination. From the Ferry-Porter law the critical fusion frequency is a logarithmic function of luminance, thus under specific conditions it can be attained that the visual sensation will be a linear function of the critical fusion frequency.

The way of obtaining the spectral sensitivity curve of the vision of a subject by means of determining the critical fusion frequency at predetermined discrete spectral wavelengths will be called critical fusion frequency scanning or CFFS method, and this forms the basic concept of the present invention.

The predetermined discrete frequencies (wavelengths), at which the critical fusion frequency is worth to be determined will be those at which the spectral sensitivity curves of subjects with differing color vision deficiencies differ from each other and from the standard curve of persons with no color vision deficiency. From the close analysis of the comparative diagrams shown in the cited paper of Wald these frequencies will correspond to the colors: blue, green, orange and red, and preferably they are narrow spectral bands centred around about 435, 535, 615 and 660 nm, respectively.

During the CFFS method respective blue, green, orange and red light emitting diodes having predetermined discrete intensity levels should provide the illumination. At each level the respective light emitting diodes must have an intensity that together determine a white light of a given color temperature e.g. 5000 K° i.e. the respective intensities are components to a white light. It is preferable, if the intensity levels follow logarithmic steps; i.e. the associated luminous sensation follows a linear scale.

The standard spectral sensation curve and the curves of subject with color sensing deficiencies will differ from each other. In a specific mode of operation the intensity of each one of the illuminating light emitting diodes is increased or decreased by an extent that corresponds to the difference between the actual and the standard curve at the corresponding wavelength and all light emitting diodes are lighted simultaneously. This light will have a specific spectral distribution, which is capable of correcting the color vision deficiency of the subject.

The color of that light can be used as a color sample for painting the glasses or contact lenses of the subject. In a preferable embodiment a diapositive picture is taken from this light on a film which should be at least as large as the lens of an eyeglass. After processing, the thin layer that carries the color information is removed from the film and inserted between two layers of a multi-layered lens. The subject can use these glasses to compensate his or her color vision deficiency.

According to a further embodiment, the RGB co-ordinates of the compensating color will be determined, and the spectral distribution of the color transmission function of a color display is modified to correspond to this function. As a result, the pictures displayed on the screen will have colors that provide a normal color sensation to the subject.

The invention will now be described in connection with preferable embodiments, wherein reference will be made to the accompanying drawings. In the drawing:

FIG. 1 shows the schematic top view of the optical unit 10 with removed cover;

FIG. 2 shows the side view of the optical unit 10;

Figure 4:
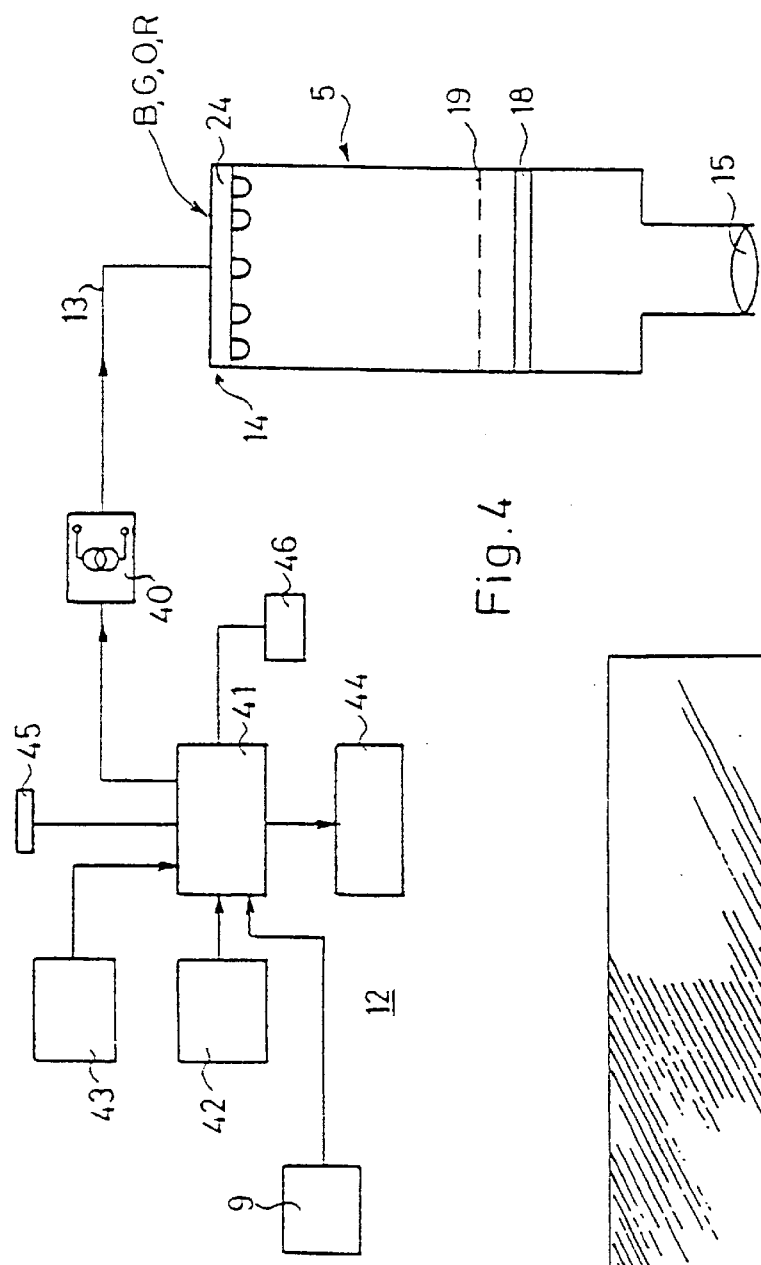
FIG. 4 shows the electrical block diagram of the control unit 12.

The apparatus for measuring the spectral sensitivity of color vision comprises two main units, i.e. optical unit 10 and control unit 12 (FIG. 4). The optical unit 10 is shown in FIGS. 1 and 2 and it is arranged in a closed rectangular housing 2. Adjustable mounting bracket 1 is extending out from the bottom plate of the housing 2 in downward direction for establishing a pivoted connection to a support stand (not shown) to enable free adjustment of the height and inclination of the housing 2. The adjusted position can be fixed by bolt 3. A rubber mask 4 is fixed to the faceplate of the housing 2 and designed to abut and shield the face of the subject under test, at least in a region around the eyes when the face is pressed against it. The mask 4 has the task of keeping light out of the eyes of the person under test, which shortens the time required for adaptation.

Figure 3:
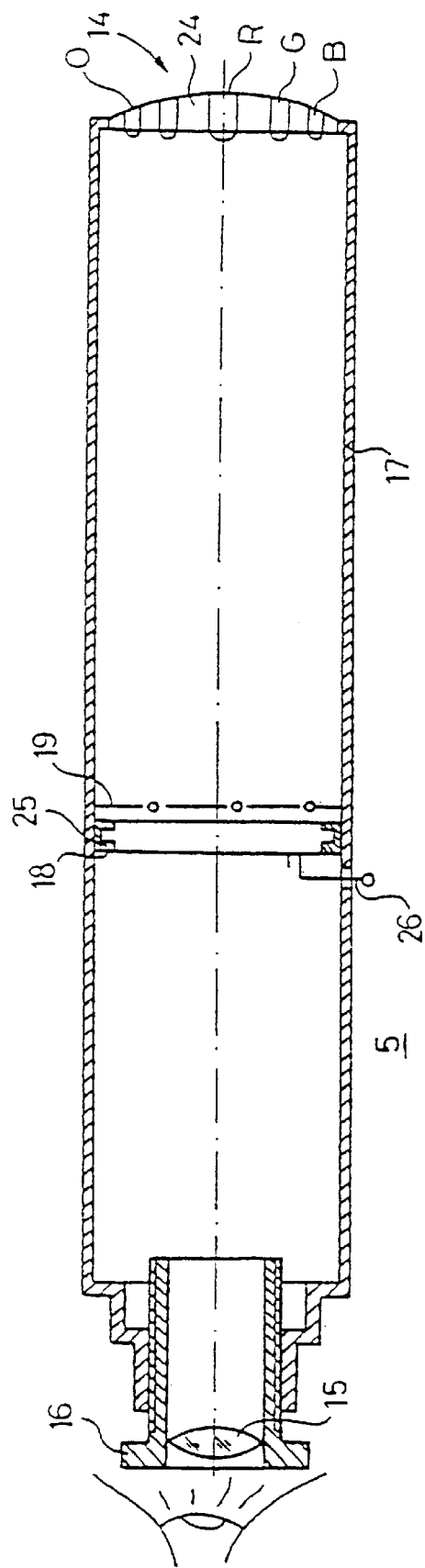
FIG. 3 shows the sectional elevation view of the sliding assembly 5.

In FIG. 1 the optical unit is shown with removed cover, and a sliding assembly 5 is guided for transversal movement by bars 6 and 7 as indicated by arrow 11 in FIG. 1. Turning wheel 8 of a precision potentiometer 9 is extending out of the left side of the housing near to the faceplate. The potentiometer 9 is used for adjusting the flicker frequency of the light generated. Flexible wire 13 is coupled to the rear side of the sliding assembly 5 and provides control and supply voltages for the light sources arranged in the rear portion of the sliding assembly. The sliding assembly 5 shown separately in FIG. 3 is an elongated hollow tube 17 with rectangular cross section, which has a lighting unit 14 at the rear end and an ocular lens 15 at the frontal end. The lens 15 is fixed in sleeve 16 that has a threaded axial portion fitted in the frontal narrow end of the tube. The axial lens position can be adjusted by rotation of the sleeve 16. A transversal slot 18 is defined at the top of the tube 17, which enables insertion of a slide 25 into the interior of the tube 17. The top of the housing 2 is also provided with a narrow opening (not shown) just above the slot 18 to enable insertion and removal of the slides according to the requirements of the test program. At the bottom part of the slot a plurality of contacts 26 are arranged, which have the task of contacting a code area on the frame of the slide to be inserted. The slides are provided with a coded combination associated with the type of the slide. The contacts 26 deliver information on the actual code of the slide towards the microprocessor in the control unit 12. Closely behind the slot 18 towards the lighting unit 14 a screen 19 is provided which extends in transversal direction and it is made of a mat and transparent sheet material e.g. glass or paper and this acts as a diffuser for the incident light.

The lighting unit 14 comprises a plurality of light emitting diodes (LEDs) B, G, O and R with colors blue (435 nm), green (535 nm), orange (615 nm) and red (660 nm), respectively. The diodes B, G, O, R have cylindrical design with a diameter of 5 mm and they emit light with an angle of divergence within the range of about 15–30°. The LEDs are arranged on a mounting plate 24, and the required luminous intensity can be attained if a plurality of LEDs is used for almost each color. In case of the blue LEDs B respective color filters (not shown) are arranged across the path of the emitted light, since blue LEDs with the required narrow radiation band and intensity (above 1 Cd) are commercially not available.

The preferred radiation bandwidth can be provided by means of using an appropriate band-pass filter e.g. sheet glass type BG-24 or BG-25 of the German company Schott Glasswerke AG. The LEDs are arranged symmetrically in the mounting plate 24, and they are directed towards the centre of the screen 19. The distance between the lighting unit 14 and the spatial radiation angle of the LEDs has been chosen in such a way that the light spot of each diode on the screen 19 will have a substantially even distribution.

FIG. 4 shows the electrical block diagram of the control unit 12. The light emitting diodes (or the groups of them with identical color) are coupled through the flexible wire 13 to respective current generators of a current generator circuit 40. Each current generator is associated therefore with one of the four colors B, G, O and R, and they are of the type, that the current value they are passing through the associated diode(s) can be determined by means of a central microprocessor 41. The microprocessor 41 is connected with a ROM memory 42, a keyboard 43 and with the potentiometer 9 of the optical unit 10. The microprocessor 41 controls a display 44, which provides visual information to the practitioner leading the tests. The microprocessor 41 can be coupled to a data line or to a printer through port 45 to deliver information on the test results either in the form of a printed document or as data file. An actuator 46, usually made by a joy-stick is coupled to the microprocessor 41. The firing button at the top is pressed by the subject when fusion is detected, while the left and right movements are used for moving the sliding assembly in left and right direction to position it opposite to the left and right eyes, as required.

The operation of the apparatus and the test function performed are as follows.

First, the basic principles of operation and the calibration of the apparatus will be described. It has been found that sufficient accuracy can be attained if the lighting unit 14 is capable of providing nine discrete levels of intensity. The highest intensity belongs to level 9, while the lower to level 1. At the calibration process level 9 is adjusted first. Current is passed through all light emitting diodes B, G, O and R, and the color temperature and the luminous intensity of the mixed output light are detected. A white light of about 4500–5000 K° color temperature is adjusted so that the intensity of the light will be close to the permitted maximum of the diodes. This will be level 9 for the white color. Since the white color was obtained as a mixture of the four components, level 9 for the respective blue, green, orange and red diodes will be the corresponding component intensity. The respective current values of the four diode-groups are written in the memory 42 for level 9. The lowest level 1 should be about 35–40 lux, because this is about the lowest level at which color sight tests can be carried out. At this level the same procedure is carried out, i.e. a white light with the predetermined color temperature is generated with an intensity of about 40 lux. The four driving current values will be level 1 for the four diode-groups, and these current values will be stored in the memory. The intensity range defined between levels 9 and 1 is divided to eight sub-ranges in such a way that the quotients of subsequent sub-ranges will be the same, which means that the logarithmic values of the intensities of the ranges determine a linear scale with identical steps. It is known that the sensation of luminous intensity is proportional to the logarithmic value of the actual intensity, thus our levels give a sensation of equal gradation. As a result, the memory will store 9×4=36 current values.

Figure 5:
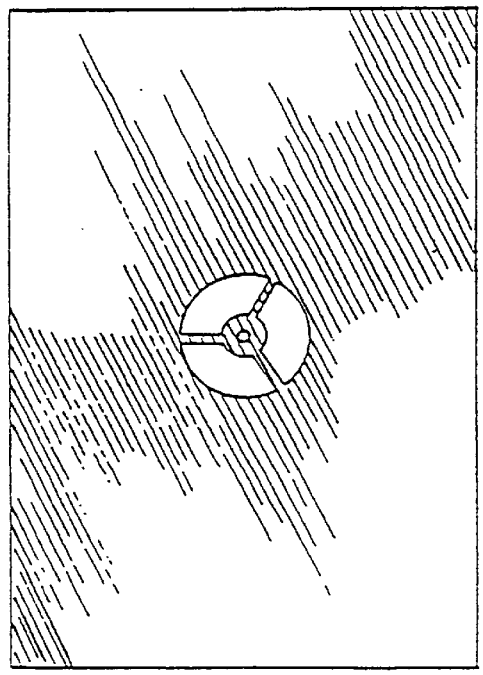
FIG. 5 shows the pattern of the slide used for CFF measurements.

The critical fusion frequency measurements are carried out in such a way that a slide having a special test pattern is inserted in the slot 18, i.e. across the light path. The test pattern is shown in FIG. 5 and comprises a non-transparent (black) basic field and three discrete transparent segments of a circle, each being 120° wide and a small transparent spot in the center. The outer diameter of the transparent segments is selected in such a way that the viewer can see it under an angle of 1.8° to 2°. The inner diameter of the transparent field is about 0.8°. In the center the small white spot serves as fixation point for the eye and it is very small. The reason of using this specific geometry is that our test requires that only those areas of the eye can get light, where cones provide visual sensation only. In fields other than specified here, rods have also role in perception. Since rods are more sensitive than cones, their stimulation could give false values for the critical fusion frequency.

When the subject pushes his face and template to the mask 4, he is asked to adjust the position of the sliding assembly. It can be moved in transversal direction by means of the actuator, and the person under test can adjust its position in the optical axis of his left or right eye. He can also adjust the sharpness of the figure by means of changing the position of the lens 15 by rotating the sleeve 16. The lens 15 is designed to compensate hypermetropia or myopia up to about 8 dioptries, therefore the subject need not use glasses. The human eye requires about 30 seconds to adapt to a new intensity level. After this time has elapsed, the critical fusion frequency will be determined for white light, which has a medium intensity corresponding e.g. to level 5. The light is made to flicker with an equal ratio of the on and off times. The frequency can be changed freely by means of the potentiometer 9. After the half minute long adaptation time the subject tries to determine the fusion frequency and pushes the button of the actuator 46 when he sees no more flicker. The actual frequency is read in the memory. The fusion frequency is measured for the left and right eyes separately and preferably twice. The program disregards the first two measurements and forms the average of the last two ones.

The critical fusion frequency determined for the white color will form a unity value for each test person, since the absolute value depends on numerous factors including age, general condition, sex, etc and it differs from person to person. All critical fusion frequency values will thereafter be expressed as percentages of the value obtained in case of white measurements. By such a normalization the test results will be objective and appropriate for comparison.

Before going on to the color CFFS measurements, a conventional color vision is carried out. We have produced respective color slides from the color vision tables referred to in the description of the prior art portion of the present specification. Each slide bears a serial number, which is equal to the number of the associated table. The frame of the slides is provided with a coded combination of electrically conductive zones, which engage contacts 26, thus the microprocessor 41 is informed on the serial number of the table used. The pattern embedded in the color slide is a number, which is also stored in the memory in an address associated with the serial number. The color vision test is carried out as in case of conventional tables, i.e. first those slides are inserted which correspond to the basic types of color vision deficiencies. The practitioner, who guides the test, is informed on the serial number of the slide actually in use, and the display informs him on the correct answer. The subject under test will report the number detected, and this number will be stored in the memory. By the end of the color vision test, the practitioner will know whether the subject has color vision deficiency just as in case of conventional measurements. The slides are illuminated with white light of level 5.

Figure 6:
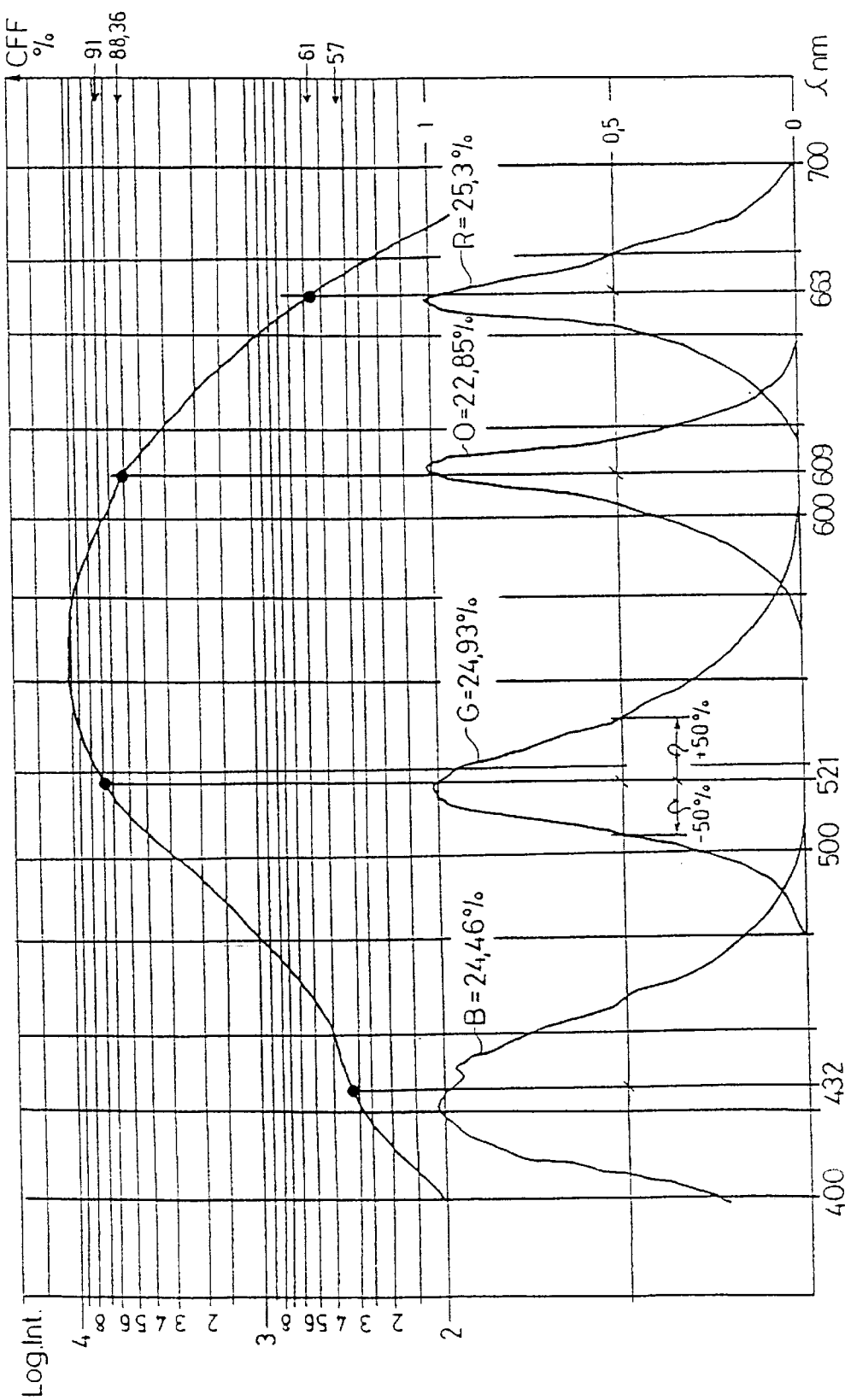
FIG. 6 shows the normal sensitivity curve and the spectral distribution of the four light sources.

The critical fusion frequency measurements are carried out for each one of the four colors blue, green, orange and red driven at level 5. The slide with the pattern shown in FIG. 5 is used. At least two measurements are used for each color involving the left and right eyes, and the average of the critical fusion frequencies is stored in absolute value (Hz) and in relative value, i.e. divided by the CFF value for the white light of the same level. The four numbers obtained is characteristic to the color vision properties of the subject under test. For the sake of illustration FIG. 6 shows the normal spectral sensitivity curve of persons with correct color vision. Such a curve is often referred to in the literature as "normal foveal sensitivity". The curve is depicted from the Wald article referred to hereinabove. The horizontal axis shows the wavelength in a linear scale in nm units. The ordinate is a logarithmic scale of the luminous intensity, and at the same time it is linear for the critical fusion frequency (CFF) which is shown at the right side of the diagram. Just below the sensitivity curve the spectral distribution of the four light sources are shown. The green, orange and red curves are properties of the light emitting diodes applied, while the blue curve has been obtained by using the blue filter in front of the diodes.

The drawing shows the intensity weight of the individual light sources, which means that the white color of unity intensity uses 24.46% energy from the blue, 24.93% from the green, 22.85% from the orange and 25.3% from the red light sources. The dots show measured CFF values for the four light sources, they all lie on the normal foveal sensitivity curve.

To prove that the foveal sensitivity curve can be obtained from narrow band critical fusion frequency measurements, in a test equipment six light sources with six wavelengths were used. The measured values in all six points fell in the normal foveal sensitivity curve, thus this curve can be obtained by means of the novel method i.e. using critical fusion frequency scanning. It was explained in an earlier part of the specification that the different sensitivity curves taken from persons having color vision deficiencies differ from the standard curve most characteristically at the chosen four wavelengths i.e. at blue, green, orange and red. Therefore, it is sufficient to use these four colors for the tests and for the compensation of the deficiencies.

For the evaluation of the results obtained from CFFS measurements it was important to determine the tolerance ranges in the normalized critical fusion frequency values (NCFF values) for each of the four colors. CFFS tests were carried out on a group of volunteers with correct color vision, and it was obtained that in more than 95% of the cases the NCFF values were within the following ranges:

Blue: 54–62%; Green: 87–95%; Orange: 78–83%; Red: 59–65%

Figure 7A:
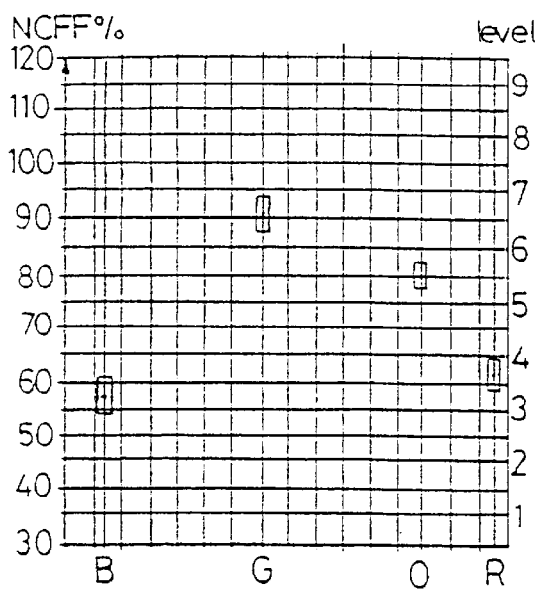
FIGS. 7a to f are simplified spectral curves showing exemplary test results.
Figure 7B:
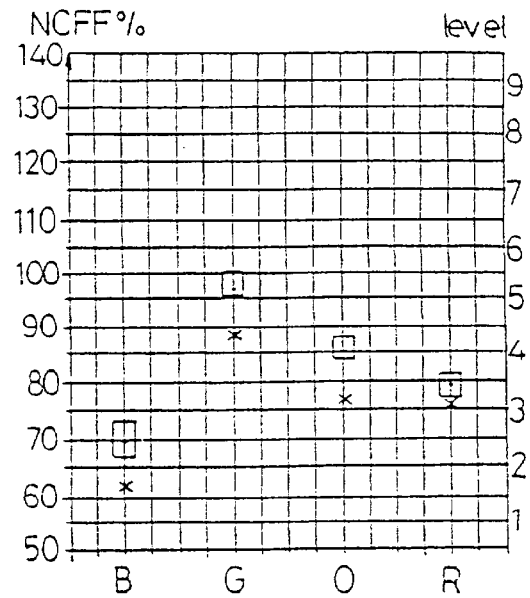
Figure 7C:
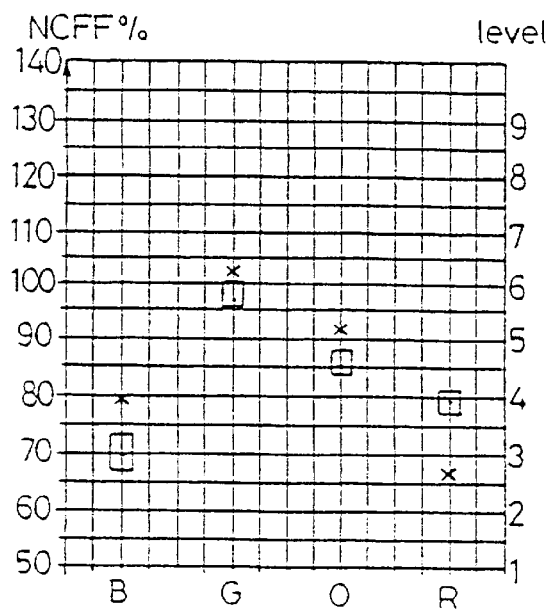
Figure 7D:
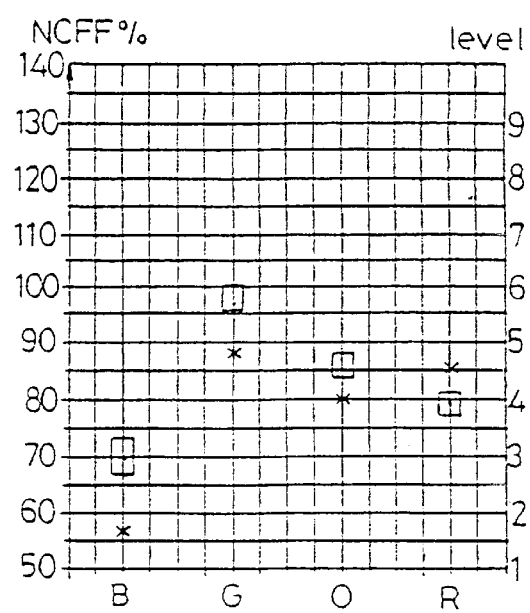
Figure 7E:
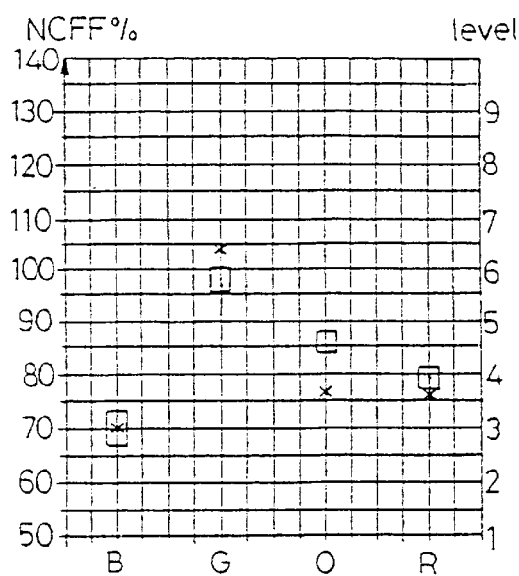
Figure 7F:
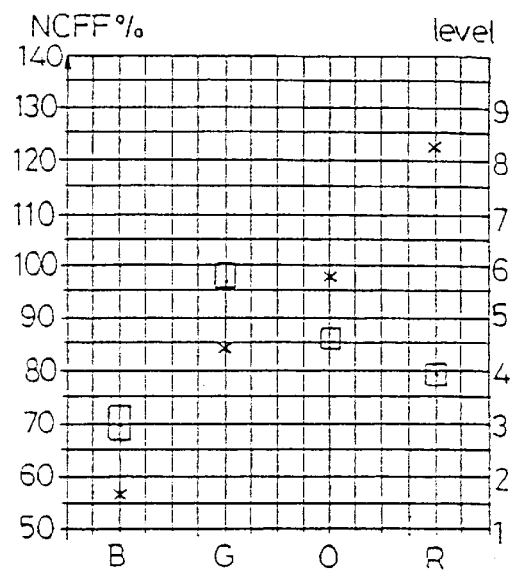

FIG. 7a shows these data in a small co-ordinate system, in which the vertically extending rectangles at each discrete wavelength indicate the associated tolerance range. The left vertical axis shows the normalized critical fusion frequency value in percent, and the right scale running from 1 to 9 shows the intensity levels of the light sources.

When carrying out the CFFS measurements, a test sheet was produced used at each measurements, which comprised the diagram of FIG. 7, the name and age of the patient, the date, the serial number of the sight test tables associated with a + or a − sign indicating whether the embedded number was recognized correctly or not, the measured critical fusion frequency at each color in Hz and in normalized value.

FIGS. 7b to 7f show five exemplary test diagrams of our measurements, wherein each person has a color vision deficiency. The test program was carried out on students of 11 to 14 years, selected as having color vision problems established in a regular ophthalmic screening. The screening concerned more than thousand students, and the number of selected students was 41. In case of FIG. 7b the student's CFF values were well below the standard one for the first three colors, and he could not identify tables 7 to 9, 15 and 17. The diagram shown in FIG. 7c belongs to a child who could not identify tables 3 to 8, 10 to 14 and 17. The diagram of FIG. 7d belongs to a green-red daltonian, who could not identify tables 2 to 8 and 17. The diagram of FIG. 7e belongs to a green-red daltonian, who could not identify tables 4 to 7, and 9 to 12. The diagram of 7f relates to a patient probably without green receptors, and this is a color blindness, which cannot be compensated or corrected.

With the apparatus shown, we have used the same level of intensity for each color, which was used when the critical fusion frequency was measured for white light. The diagrams of FIG. 7 demonstrate that in case of color vision deficiencies, the measured CFF values lie outside the allowable tolerance range indicated by the vertical rectangles. If the intensity of a color is decreased or increased in such an extent that corresponds to the difference from the measured value from the allowable range, then the critical fusion frequency at that particular color will be within the standard range. In the diagrams of FIG. 7 the intensity is shown in level units, and the practitioner can determine how many levels he should add or deduct from the intensity of each color to bring the CFF value in the normal range. In case of the patient, whose diagram was shown in FIG. 7b the colors blue, green and orange were increased to level 6, and the red was left at level 5. The dots in the diagram show the associated CFF values, which are now within the acceptable range. The color, obtained when all the four light source is illuminated, will not be white any more, it will have a special spectral distribution which will be called as compensating light and it has a compensating color.

By using the compensating color, the test with the color slides carrying the test tables was repeated. The child could recognize all embedded patterns, i.e. his color vision defect has been compensated. Similar compensation was carried out for all patients examined, and with the exceptions of a few students, the color vision problems have all been overcome i.e. compensated. In a later ophthalmic examination it became clear that those students had other eye problems. In this way the color vision problems shown in FIGS. 7b to e were compensated, only the color blindness shown diagrammatically in FIG. 7f remained unchanged.

The compensation is specific for each person, since the intensities of the component colors are adjusted according to the measured sensitivities, thus the color by which the problems can be overcome has been determined. The check by transilluminating the test slides constitutes at the same time proof and safety for the compensation, which is similar to the use of a new glass during an examination, which makes him possible to see the test board clearly.

The question arises, how can it be possible to apply the compensating color. There are several ways, how this objective can be achieved. There are several technologies by which optical glasses and contact lenses can be painted. Most of these technologies use the standard color numbers (or tests sheets including sample colors) as samples, on the basis of which the associated color can be made. The human eye works very well in comparing two colors or shades of the same color. The apparatus provides the sample color, and this can be used for the comparison. In an optical workshop it is too expensive to use a complete examination and test device as described. To that purpose a simplified version is sufficient, wherein the optical unit generates the compensating color on a screen that can be looked at directly. If the four level data of the compensating color are read in the apparatus used in the workshop, the same compensating color can be generated at this remote location.

A simple but efficient way of making eyeglasses with the compensating color is the photographic reproduction of the compensating color. If a diapositive picture is taken from the screen of a laboratory unit, then the color of the developed film will be the compensating color. There are technologies by which the thin color carrier layer can be separated from the developed film. It has been found that the soaking of a film in a ketone, e.g. chloroform in a closed place and through a considerable time will result in the automatic peeling off of the color layer from the carrier celluloid substrate. The eyeglass should be made of two parts united by a transparent adhesive bond in such a way that the thin color carrier layer is placed on the first part, and the second part is pressed against is. A small amount of adhesive should be placed on both glass parts. The thin layer will thereafter remain embedded between the two glass parts, and the light passing through the glass will have the required compensation.

The attenuation of such filters is rather small, generally it causes an intensity loss of about 10–20%, which is insignificant and much less than in case of using prior art color filters. The difference with the prior art filters lies in that the compensation takes the whole visual spectral range into account, and it may not happen, that the red portion of the full range is compensated, however, the correct vision in an other range is still not ensured. Color sight tables are not appropriate to discover color vision problems in the blue range.

A further way of compensation can be made in an electronic way. The intensities of the components of the compensating color are known, as well as the difference relative to the white light. Electronic display means have a video color channel with a predetermined transfer function. If this function is modified in such a way that the transmitted color signals be transformed according to the modified color, then the pictures displayed on the screen will have correct color balance in the eyes of the person, whose compensation color was used. In this way they can use television, computer monitors as if they had normal color vision. If more than one person uses a display, the portable remove controller should be provided with color storage and retrieval function, whereby the compensating color of the required number of persons can be achieved.

What is claimed is:

1. Method for detecting color vision properties of a subject by determining his or her spectral sensitivity curve, characterized by carrying out said determining step by critical fusion frequency scanning, wherein the critical fusion frequency is measured with a discrete number of color lights radiating at respective narrow wavebands, and each of said color lights have an intensity that corresponds to the component intensity of a white light with a predetermined color temperature in said narrow waveband of said color light.

2. The method as claimed in claim 1, wherein the combined light of all of said color lights results in said white light, and the method further comprising the steps of measuring the critical fusion frequency of said combined light, and calculating the quotients of the component critical fusion frequency values and of the critical fusion frequency of said combined white light to obtain normalized critical fusion frequency values, and using said normalized critical fusion frequency values at said determining step.

3. The method as claimed in claim 2, wherein the color of said light sources being blue, green, orange and red with respective medium wavelengths being about 435, 535, 615 and 660 nm.

4. The method as claimed in claim 2 for obtaining the compensation color of the determined vision deficiency, characterized by the steps of establishing the differences between a standard spectral sensitivity curve determined previously from subjects with normal vision and the curve of the subject under test at each of said bands, and in the bands where a difference has been established, increasing or decreasing the intensity of the associated light source corresponding to the extend and sign of said difference, and generating said compensating light by simultaneously illuminating all of said light sources with the so adjusted intensity.

5. Method for providing a correction lens for a subject with color vision deficiency by utilizing the compensation color as determined by claim 4, characterized by the step of painting said lens by means of a conventional lens painting method using said compensation color for defining the color of the painting.

6. Method for providing a correction lens for a subject with color vision deficiency by utilizing the compensation color as determined by claim 4, characterized by the steps of: taking a diapositive picture of said compensating light, separating the color layer from the diapositive, inserting said color layer between two parts of a glued lens, and connecting said parts together so that said layer gets sandwiched therebetween.

7. Method for correcting the color vision deficiency of a subject when viewing a color display by utilizing the compensation color as determined by claim 4, characterized by the step of modifying the color transfer function of said display in accordance with said compensation color.

8. Apparatus for carrying out the method as claimed in claim 2, characterized by comprising a lighting unit (14) composed of light emitting diodes (B, G, O, R) or groups thereof emitting light in said bands, respectively; a hollow tube (17) receiving said lighting unit (14) at one end region; an ocular lens (15) arranged at the frontal other end of said tube; a diapositive slide arranged across said tube and having a transparent pattern allowing passage of light towards those parts of the retina of the subject looking through said lens, where vision is provided purely by cones; a current generator circuit (40) including respective controlled current generators associated with said diodes (B, G, O, R), a pulse generator coupled to control inputs of said current generators for controlling pulsation of current flowing through said diodes; and a potentiometer adjustable by the subject under test for adjusting the repetition frequency of said pulse generator.

9. The apparatus as claimed in claim 8, wherein the currents of said current generator circuit (40) are adjustable in separate predetermined steps for each of said light sources, and the currents at each step being interrelated in such a way that the simultaneous illumination of all diodes result in a white light with a predetermined color temperature.

10. The apparatus as claimed in claim 9, wherein said steps correspond to equal intensity step sensations by the subject when viewing the light generated by the excitation of said diodes by said currents.

11. The apparatus as claimed in claim 8, further comprising a display (44) providing information on the results of the examinations, a keyboard (43) for adjusting the mode of operation, a microprocessor (42) for controlling and coordinating operation, and a memory (42) for storing actual values of the critical fusion frequency of the subject at each measurement as well as for storing normalized values of said critical fusion frequencies relative to a basic critical fusion frequency obtained by illumination with white light.

12. The apparatus as claimed in claim 8, comprising a set of color slides that can be inserted in the place of said diapositive slide, said color slides comprise standard tables for testing color vision.

13. The method as claimed in claim 1, wherein said critical fusion frequency measurements being carried out when the eye of the subject has adapted to the actual intensity used, and the light of said light source being directed to areas of the retina where there is a pure cone vision.

* * * * *